United States Patent [19]

Foster et al.

[11] 4,310,985
[45] Jan. 19, 1982

[54] DEVICE FOR COMBATTING FLIES

[75] Inventors: James P. Foster, Modesto; Walter T. Reed, Oakdale, both of Calif.

[73] Assignee: Shell Oil Company, Houston, Tex.

[21] Appl. No.: 103,323

[22] Filed: Dec. 14, 1979

[51] Int. Cl.³ .............................................. A01M 1/20
[52] U.S. Cl. ..................................................... 43/131
[58] Field of Search ................. 43/107, 114, 118, 121, 43/122, 129, 131, 132 R; D22/19

[56] References Cited

U.S. PATENT DOCUMENTS

| D. 247,249 | 2/1978 | Schimanski | D22/19 X |
|---|---|---|---|
| 1,056,535 | 3/1913 | Grimes et al. | 43/131 |
| 1,262,790 | 4/1918 | Hengstenberg | 43/131 |
| 1,573,278 | 2/1926 | Schlesinger | 43/131 |
| 1,672,576 | 6/1928 | Meyer | 43/121 |
| 2,167,978 | 8/1939 | Jennerich | 43/131 |
| 2,234,500 | 3/1941 | Moore | 43/131 X |
| 2,254,948 | 9/1941 | Kubalek | 43/131 |
| 2,956,366 | 10/1960 | Wiesmann | 43/131 |
| 4,065,560 | 12/1977 | Powell | 424/246 |
| 4,160,335 | 7/1979 | Von Kohorn et al. | 43/131 |

Primary Examiner—James M. Meister
Assistant Examiner—Robert P. Olszewski

[57] ABSTRACT

A device for combatting troublesome flying insects comprising a sloped target area containing a wet or dry dosage of tetrahydro-2-(nitromethylene)-2H-1,3-thiazine lethal to flies and covered with a closely fitting or flush grill; a hollow base section having a bottom and side or sides; a cavity for the containment and concealment of intoxicated flies; and a means of supporting said target area. In the case where the device contains a wet amount of said insecticide, the device further contains a means of establishing fluid contact between the target area and a fluid reservoir in the base section. Also claimed is a method for combatting flies utilizing the devices of the invention.

13 Claims, 7 Drawing Figures

DEVICE FOR COMBATTING FLIES

BACKGROUND OF THE INVENTION

This invention relates to a device for combatting troublesome flying insects. More particularly, this invention is directed to a device comprising a sloped target area containing a wet or dry dosage of tetrahydro-2-(nitromethylene)-2H-1,3-thiazine lethal to flies, and covered with a closely fitting or flush grill; a hollow base section having a bottom and side or sides; a cavity for the containment and concealment of intoxicated flies; and a means of supporting said target area. In the case where the device contains a wet amount of said insecticide, the device further contains a means of establishing fluid contact between the target area and a fluid reservoir in the base section.

Certain 2-(nitromethylene)-1,3-thiazines and derivatives thereof are disclosed in U.S. Pat. Nos. 3,993,648 and 4,065,560 as having useful insecticidal activity and as acting very quickly on the house fly (*Musca domestica*). While the insecticidal activity of tetrahydro-2-(nitromethylene)-2H-1,3-thiazine is specifically disclosed, the compound is not included in the class of compounds with quick action (knockdown) against the house fly. In this context, it should be noted that a compound with fast knockdown times toward a particular insect does not necessarily also possess high insecticidal activity (toxicity) toward the same insect. The insecticidal activity of tetrahydro-2-(nitromethylene)-2H-1,3-thiazine toward the house fly as well as the knockdown times of various other nitromethylene heterocycles are disclosed in *Pesticides and Venom Neurotoxicity*, D. L. Shankland et al. (editors), pages 153–69 (1978). The physical, chemical and insecticidal properties of these compounds are further disclosed in *Advances in Pesticide Science, Part 2*, H. Geissbuhler et al. (editors), pages 206–17 (Symposia Papers from Fourth International Congress of Pesticide Chemistry, July, 1978).

A fly such as the house fly is believed to activate its feeding mechanism after receiving appropriate stimuli via chemoreceptors believed to exist on its tarsi. The feeding mechanism then involves a process wherein the fly lowers its proboscis to the surface upon which it has landed, expels saliva through the proboscis and finally sucks back whatever solution results. This process is believed to be automatic when the fly lands on an appropriate surface.

Insect traps and devices are claimed in a number of issued patents. For example, U.S. Pat. No. 2,956,366 discloses a device for combatting flies consisting of moist, dark, flat discs or strips containing a water-soluble stomach poison, a foodstuff and optionally also a contact poison. U.S. Pat. No. 2,255,360 discloses an insecticide holder stationed above a hollow base with downwardly sloping sides. U.S. Pat. No. 1,056,535 discloses a fly killer which uses a capillary member or wick to draw water from a tray up to a fabric pad containing dry poison which is covered with a grid. Insect devices incorporating a means of supplying an aqueous solution of insecticide to a porous target area are additionally disclosed in U.S. Pat. Nos. 1,902,723 and 1,916,982. Other U.S. Patents which disclose insect-combatting devices include the following: U.S. Pat. Nos. 3,959,914; 3,855,727; 3,807,081; 3,653,145; 2,606,391; 2,097,924; 1,797,743; 1,672,576; 1,572,098; 1,482,992; 1,289,466; 1,200,993; 280,291 and U.S. Design Pat. No. D. 232,829. However, the listed patents do not describe the novel combination of features presently claimed nor the use of the present insecticide in the manner hereafter characterized.

SUMMARY OF THE INVENTION

A device has now been discovered which is very effective in combatting a variety of troublesome flying insects, such as flies of family Musca, including the house fly (*Musca domestica*) and the bush fly (*Musca vertustissima*), as well as flies of other families, such as the blow fly (*Calliphora vomitoria*), the fruit fly (*Drosophila melanogaster*) and the stable fly (*Stromoxys calcitrans*). The device is particularly effective in combatting the house fly. As one aspect of the invention, referred to as a wet trap, the device comprises:

(a) a target area of porous material comprising a sloped surface containing a dosage of tetrahydro-2-(nitromethylene)-2H-1,3-thiazine insecticide lethal to flies, (b) a closely fitting or flush grill covering said target area but allowing contact by the flies thereon, (c) a sloped supporting member for said target area comprising a solid sheet of rigid impermeable material shaped to conform with the shape of the target area and having its upper surface affixed to the target area so as to support and define the configuration of the target area, (d) a hollow base section having a bottom and side or sides surrounding the bottom and perimeter of said sloped target area supporting member, the sides or sides of said base section extending up a sufficient distance to form a cavity between the side or sides of the base and the target area supporting member, said cavity being of sufficient size for the containment and concealment of intoxicated flies; the base section being attached to the sloped supporting member such that a refillable reservoir for fluid storage or containment is formed in the hollow base section, said reservoir being defined on its top by the sloped supporting member and on its bottom by the bottom of the base section, and (e) a means of establishing fluid contact between said target area and said refillable reservoir.

As another aspect of the invention, referred to as a dry trap, the device comprises:

(a) a target area comprising a sloped surface containing a dosage of tetrahydro-2-(nitromethylene)-2H-1,3-thiazine insecticide lethal to flies, (b) a closely fitting or flush grill covering said target area but allowing contact by the flies thereon, (c) a hollow base section having a bottom and side or sides surrounding the bottom and perimeter of said target area, the side or sides of said base section each extending up a sufficient distance to form a cavity around and/or under said target area, said cavity being of sufficient size for the containment and concealment of intoxicated flies, and (d) a means of supporting the target area within or above said base section which allows sufficient clearance between the side or sides of the target area and the upwardly extending side or sides of the base section for the intoxicated flies to pass into said cavity for containment and concealment.

As yet another aspect of the invention, a method is described for combatting flies utilizing either of the above devices.

The invention is based in part on the findings that tetrahydro-2-(nitromethylene)-2H-1,3-thiazine (TNMT) possesses both fast knockdown times and high insecticidal activity against various flies. Because of these features of TNMT, as well as its high water solubility, a lethal dose of the insecticide is ingested by a fly in which the feeding mechanism is activated while upon the target surface of the device. The intoxicated fly then rolls down the sloped target area toward the base section and is contained out of view; concurrent with the fast, effective action of the device, this represents an important advantage from the standpoint of consumer acceptability. The TNMT insecticide has also been found to be surprisingly stable as used herein, with the result that the device is long-lasting and thereby economical. Furthermore, the insecticide has a low repellancy toward such flies, so that the insects may easily be attracted to and/or induced to feed while on the target area of the device. The aforementioned combination of attractive features renders TNMT surprisingly effective and unique among related substituted nitromethylene thiazines as a toxicant/knockdown agent in wet or dry fly traps.

DESCRIPTION OF THE PREFERRED EMBODIMENTS

The target area of the device is the surface containing the TNMT insecticide in wet or dry form and thus the surface upon which the flies must land and feed in order to become intoxicated. In the wet trap, the target area may be composed of any porous material such as felt, muslin, cloth, or blotter paper. In the dry trap, the target area may be composed of any of the above materials or other suitable non-porous materials such as metal or plastic. In both cases, a dull or less reflective target area surface is preferred over a shiny or more highly reflective surface. The target area is preferably dark colored, most preferably black. Thus, a dull black target area is most preferred, since these attributes are believed to aid in attracting the flies to the device. The target area may be of any size, but more preferably its surface area is between 5 and 94 square centimeters. The surface of the target area should be sloped sufficiently downward so that the intoxicated flies roll toward the cavity for their containment and concealment. The target area may be curved or slanted or its sides may meet in a point, such that its vertical cross-section may range from a triangular to a semi-circular configuration. A target area with curved sides, i.e. semi-circular or semi-elliptical vertical cross-section, is more preferred.

In both the wet and dry trap, the target area is covered with a closely fitting or flush grill. The grill should allow contact by the flies on the target area and therefore will contain openings of a size sufficient to permit the flies to land and feed on the target area surface. However, the main function of the grill is to prevent accidental contact of the target area by humans, domestic pets, etc. and the grill openings are suitably limited to a size which accomplishes this function. Furthermore, the thickness of the grill is suitably limited such that the depth of the openings therein does not interfere with the roll off of the intoxicated flies into the cavity for their containment and concealment. A grill with a thickness of one millimeter or less is preferred. The grill is preferably dark colored and more preferably the same dark color as the target area. As stated, the grill may be flush with the target area; alternatively it may be fitted within a distance close enough to the target area to allow a fly standing on the highest portion of the grill to reach and ingest some of the toxicant on the target area surface. A grill flush with the target area is preferred, since the dead flies will then be more likely to roll into the cavity described above instead of becoming potentially entrapped between the grill and target area surface.

The wet trap contains a sloped supporting member for the target area. The supporting member comprises a solid sheet of material impermeable to liquids and the TNMT insecticide. For ease of manufacture and economy, it is preferred that the supporting member be constructed of the same material as the base section discussed more fully below, i.e. preferably a commercially available polyolefin. The material used to construct the supporting member is rigid and conforms with the shape of the target area, having its upper surface affixed to the target area, so as to support and define the configuration of the target area. The target area is suitably attached to the supporting member by means of hooks on the upper surface of said supporting member; the target area need not necessarily cover the entire upper surface of the supporting member. The grill which fits upon the target area is suitably held in place by means of the same hooks.

In the wet trap, the bottom and perimeter of the target area supporting member are surrounded by a hollow base section having a bottom and side or sides. The side or sides of the base section extend upward a distance sufficient to create a cavity between the side or sides of the base and the target area supporting member, preferably the side or sides of the base section will extend up to or slightly above the level of the uppermost portion of the target area. The cavity is of sufficient size for the containment and concealment of intoxicated flies when they roll down the sloped surface of the target area. Preferably, the cavity will extend around the entire perimeter of the target area supporting member, so as to contain and conceal a greater number of flies. The side or sides of the base section may abut the sloped surface of the target area; more preferably, the side or sides of the base will be at a sufficient distance from the perimeter of the target area and its supporting member such that the cavity for containment and concealment of intoxicated flies is defined on its bottom by the bottom of the base section; most preferably, there exists a distance of about one centimeter between the lowermost perimeter of the supporting member and the side or sides of the base section. Optionally and preferably, in both the wet and dry traps, the upper portion of the side or sides of the base section may bend inward to form a lip that further conceals the flies in said cavity, provided however that sufficient clearance between such inwardly bending portion and the target area exists so as not to interfere with the descent of intoxicated flies down the sloped surface of the target area into the cavity for containment. In the wet trap, the perimeter of the base section will preferably be of the same general configuration as the perimeter of the target area supporting member, and more preferably, the side or sides of the base section will be equidistant from the perimeter of the supporting member, i.e. the supporting member will be centered within a larger base section.

In both the wet and dry traps the base section is suitably constructed with a variety of known materials and preferably with such commercially available polyolefinic materials as polyethylene. The base section is preferably of a shape which would allow the device as a whole to be free standing on level surfaces and therefore has a flat horizontal bottom. Its configuration is preferably box-shaped, rectangular or cylindrical, with a box shaped or rectangular configuration preferred. The base section may optionally include some conventional means of suspending the device, if desirable to utilize it in this manner. It is preferred that the base section be of a light color which contrasts with the preferred dark color of the target area. Thus, a white contrasting base section surrounding a black target area is most preferred, again since this is believed to aid in attracting flies to the device. When desired, the accumulated dead flies in the cavity for concealment and containment may be disposed of by simply inverting the device.

In the wet trap, the base section is attached to the sloped target area supporting member such that a refillable fluid reservoir is formed in the hollow base section. This fluid reservoir is defined on its top by the supporting member and on its bottom by the bottom of the base section. The base section may be attached to the supporting member in various manners; the supporting member may fit within a groove optionally provided in the bottom of the base section or may be held by a suitable glue or caulking material such that the fluid in the reservoir is held without leaking. Alternatively and preferably, there may extend upward from the bottom of the base section an interior wall or walls of the same configuration as the lowermost perimeter of the target area supporting member, upon or within which the supporting member will fit tightly, again such that the fluid in the reservoir is held without leaking. The manner in which the fluid reservoir is refilled may also vary. A resealable inlet or portal through which liquid is added may be provided for in a side or sides of the base section, provided that the liquid so added proceeds into the fluid reservoir defined above and not into the cavity for containment and concealment of intoxicated flies. Alternatively, a resealable inlet or portal may be provided for in the bottom of the base section; the device would then be inverted for refilling as necessary. In the latter case, the perimeter of said inlet or portal should be no larger than and fit entirely within the perimeter of the supporting member, again so that liquid does not enter the containment cavity. The manner in which the inlet or portal is resealable is not critical; an item which prevents the fluid from evaporating or leaking out of said inlet or portal, such as a cork, stopper or detachable panel, is preferred. Water is the fluid of choice; the fluid should contain at least some proportion of water so that a solution of the water soluble insecticide results on the target area. Other fluids, such as glycerine may also be added. The amount of water added to the fluid reservoir may vary; preferably, the amount is correspondingly larger in devices with larger target areas and is at least sufficient to keep the surface of the target area moist. A number of methods may be used to impregnate the porous surface of the target area with insecticide. For example, the target area material may be previously soaked in a solution of TNMT and allowed to dry, the surface of the target area may be painted with a solution of TNMT or TNMT may be sprinkled on the target area. The insecticide is typically applied so as to be present on the target area in the amount of at least 0.036 milligrams per square centimeter. At a minimum, the insecticide concentration on the target area must be sufficient to constitute a lethal dose when ingested by the fly. The device is periodically checked for liquid level and the fluid reservoir refilled as needed.

The wet trap further contains a means of establishing fluid contact between the target area and the refillable fluid reservoir. This may be suitably accomplished by any of a variety of conventional means which will maintain the moisture of the target area. Preferably, the target area material or a known water-wicking material, more preferably both, will extend downward into the fluid reservoir to a point below the fluid level present when liquid is added to the fluid reservoir, so as to draw the liquid up to the exposed surface of the target area. Examples of suitable water-wicking materials include felt, muslin, blotter paper or cloth; the term "water-wicking material" is intended to denote materials which exhibit similar wicking action toward whatever fluid or solution is present in said fluid reservoir. The water-wicking material, when used, is layered between the target area supporting member and the target area. That is, the upper surface of the water-wicking material will be flush with the lower surface of the target area and the lower surface of the water-wicking material will be flush with the upper surface of the supporting member. In a device incorporating the preferred means of establishing fluid contact, the construction of the device must allow for the target area and/or wicking material to contact the liquid in the reservoir. For example, sufficient clearance for the materials to pass into the fluid reservoir may be provided under or by means of slots in the side or sides of the target area supporting member. In devices including a base section with an upwardly extending interior wall or walls upon or within which the supporting member fits, the target area and/or wicking material suitably pass between said interior walls and side or sides of the supporting member. While the construction of the device should allow the means of establishing fluid contact to operate, any material(s) so contacting the liquid in the fluid reservoir are suitably held in place so as to avoid leaks or undue evaporation of the liquid through or around the material(s) during operation or inversion of the device. The moisture resulting on the target area is believed to attract the flies to the device, induce their feeding response and/or promote the takeup of a poisonous amount of TNMT. Preferably therefore, the fluid level in the wet trap is maintained so that the target area remains moist. The wet trap will, however, be useful for combatting flies even if all fluid or moisture is allowed to evaporate, since the water soluble insecticide which is used is readily dissolved by the flies' saliva.

In the dry trap, the insecticide is again contained on a target area comprising a sloped surface. The insecticide is deposited on the material used to construct the target area by the variety of methods described for the wet trap above or, more preferably, applied as component of a glaze deposited on the target area. In the latter method, the main component of such a glaze is suitably a foodstuff acceptable to the flies, preferably sugar or corn syrup, and more preferably corn syrup. The glaze optionally and preferably contains from 0 to 20% by weight of a polymeric binder, such as polyvinyl pyrrolidine, and from 10 to 26% of the insecticide. The amount of insecticide will in all cases be dependent on the size of the target area; typically at least the equivalent of 0.036 milligrams of TNMT per square centimeter of target area are applied. The amount of insecticide must again be at least sufficient to constitute a lethal dosage toward flies that feed while upon the surface of the target area. A humectant, e.g. glycerine, may also optionally be incorporated on the target area, and may be applied as such or as a component of a glaze.

The dry trap contains a hollow base section having a bottom and side or sides surrounding the bottom and perimeter of a target area supported above or within said base section. The side or sides of the base section extend upward a distance sufficient to create a cavity around and/or under the target area, preferably the side or sides of the base section will extend up to or slightly above the level of the uppermost portion of the target area. The cavity is again of sufficient size for the containment and concealment of intoxicated flies when they roll down the sloped surface of the target area. Preferably, the cavity will extend under and around the entire perimeter of said target area, so as to contain and conceal a greater number of flies. In this preferred mode, the dry trap can accumulate more intoxicated flies than a wet trap of equivalent size, since in the dry trap the cavity extends under the target area thereby including space occupied by the target area supporting member in the wet trap. The side or sides of the base section may abut the sloped surface of the target area; more preferably, the side or sides of the base section will be at a sufficient distance from the perimeter of the target area such that the cavity for containment and concealment of intoxicated flies is defined on its bottom by the bottom of the base section; most preferably, there exists a horizontal distance of about one centimeter between the lowermost perimeter of the target area and the side or sides of the base section. The perimeter of the base section will preferably be of the same general configuration as the perimeter of the target area, and more preferably, the side or sides of the base section will be equidistant from the perimeter of the target area, i.e., the target area will be supported in the center of a larger base section.

The base section of the dry trap optionally and preferably contains a removable cup or tray to hold intoxicated flies. This allows for disposing of the flies by removing and emptying said cup or tray, as opposed to the procedure above where the entire device is inverted. The removable cup or tray may be provided for by a variety of designs and suitably has a side or sides extending up a distance sufficient to hold a large number of flies. As one alternative, the upwardly extending side or sides of the base section may be composed of a separable lower and upper portion; said lower portion, defined on its bottom by the bottom of the base section, would constitute said removable cup or tray. As a further and more preferred alternative, the device may be constructed to include a separate cup or tray having a bottom and side or sides and which fits within and pulls out from the base section. In this latter case, it is preferred that the bottom and side or sides of said cup or tray are flush with the bottom and side or sides, respectively, of said base section, so as to provide the maximum possible space for the containment of the intoxicated flies. In all cases, it is preferred that the perimeter of the removable cup or tray be of the same general configuration and approach in size the perimeter of the base section, so that most or all intoxicated flies which descend into the cavity for containment and concealment are held in said cup or tray. The optional cup or tray is suitably present in dry traps described above where the side or sides of the base section do not abut the surface of the target area; i.e. where the side or sides of the base are at a sufficient distance from the perimeter of the target area such that the cavity for containment and concealment of intoxicated flies is now defined on its bottom by the bottom of said removable cup or tray.

The dry trap further contains a means of supporting the target area within or above the base section while allowing sufficient clearance between the side or sides of the target area and the upwardly extending side or sides of the base section for the intoxicated flies to pass into the cavity for containment and concealment. The preferred means of supporting the target area comprises a solid sheet of rigid material shaped to conform with the shape of the target area and attached to the upper portion of the side or sides of the base section, so as to support and define the configuration of the target area. For convenience and ease of manufacture, it is preferred that rigid material be of the same composition as the base section. As a further preferred mode, there is provided a second solid sheet of rigid material, more preferably of metal, referred to as the target area holder, which rests upon or adheres to the upper surface of the previously described solid sheet of rigid material. The target area holder is also shaped to conform with the shape of the target area, having its upper surface attached to the lower surface of the target area. The target area and preferably also the closely fitting or flush grill are attached to the target area holder, when used, by a variety of means; preferably, the outermost side or sides of said target area holder will be constructed to provide a narrow groove or lip into which the outermost side or sides of said target area and/or grill will fit and thereby be held in place. Thus in its most preferred mode, proceeding from the top to bottom of the device, the following materials will be layered in a shape which conforms with the shape of the target area: protective grill, target area, target area holder, followed by a rigid sheet of supporting material.

The preparation and insecticidal activity of the tetrahydro-2-(nitromethylene)-2H-1,3-thiazine used in both the wet and dry traps are known. The high water solubility of TNMT at room temperature promotes the fast takeup of a lethal dose by the flies when feeding and facilitates the operation of the wet trap. The compound is nonvolatile in ordinary use, thereby releasing no harmful vapors to the atmosphere. Flies are readily attracted to land and feed on the device, since TNMT has little or no repellancy toward the insects. The compound is believed to operate as a stomach poison as opposed to a contact poison, which implies that a fly must ingest some portion of the compound for it to be effective. Although TNMT is hydrolytically stable at a neutral pH, its photochemical stability in ultraviolet light is quite low. Despite this, when the compound is used as described in the present invention, the devices prove surprisingly effective for combatting flies for several months so long as the devices are not exposed to inordinate amounts of direct sunlight. Finally, while TNMT is highly active against insects, it is much less so toward higher animal forms such as rats, rabbits and other mammals. This low mammalian toxicity in conjunction with the protective grill preventing accidental contact with the insecticide-containing target area contributes to the utility of the invention and its suitability for household use without undue danger to children, domestic pets, etc.

The devices herein described optionally and preferably contain means of attracting the flies or means of triggering the feeding response of the flies and more preferably contain both. Among the previously mentioned preferred features believed to serve as means of attracting the flies are included a dark-colored target area and grill, dull target area, light-colored contrasting base section or the presence of moisture. A further preferred means of attracting the flies is the use of an attractive dosage of a sex attractant (pheromone) deposited on the target area. Muscalure (cis-9-tricosene) is the sex attractant of choice; 10 milligrams of this compound are typically applied to the target area. In its most preferred mode, the wet trap incorporates all of the above means of attracting the flies. Similarly, the dry trap in its most preferred mode incorporates all of the above means of attracting flies with the exception of the presence of moisture.

The presence of moisture was also noted above as a potential means of triggering the feeding response of the flies in the wet trap. Other such means, useful in wet or dry traps, include the use of a bait or foodstuff acceptable to said flies. The foodstuffs of choice are sugar or corn syrup, with sugar being more preferred for wet traps and corn syrup more preferred for dry traps. The foodstuff may be deposited on the target area of the dry trap as a glaze or sprinkled on the moist target area of the wet trap. Approximately 0.5 grams of foodstuff are suitably employed in a device designed for household usage where, for example, a target area of 84 square centimeters may be used. Thus, as means of triggering the feeding response of the flies, the preferred wet trap will contain sugar on the target area and the moisture will be maintained; the preferred dry trap will contain a corn syrup glaze on the target area.

The most preferred devices include both means for attracting the flies and means for triggering their feeding response. Therefore, the wet trap of choice consists in part of a dull, black, moist target area containing muscalure and sugar, which is covered with a black grill and surrounded by a white contrasting base section. Similarly, the dry trap of choice consists in part of a dull, black target area containing muscalure and a corn syrup glaze, which is covered with a black grill and surrounded by a white contrasting base section. Either device may be inexpensively manufactured and is simple and convenient to use.

The present invention also contemplates a method of combatting flies utilizing the devices described herein. The preferred methods accordingly utilize the wet traps or dry traps of choice specified above. The wet trap and method utilizing the wet trap are more preferred. The wet trap requires periodic maintenance by the user of the liquid level in the fluid reservoir to retain its maximum effectiveness, but the wet trap is also faster acting and more attractive to the flies than the dry trap. Furthermore, the wet trap will continue to function, although somewhat less effectively, even if allowed to dry out.

The devices are suitable for indoor or outdoor use, with indoor use more preferred. They represent a convenient, inexpensive and effective way of combatting a variety of troublesome flies in and around the home, barns, dairies, restaurants, warehouses and the like; wherever they swarm. The devices are safe while in operation, due to the protective grill, low volatility and low mammalian toxicity of the TNMT insecticide.

The invention will now be further elucidated with reference to the drawings.

Figure 1:
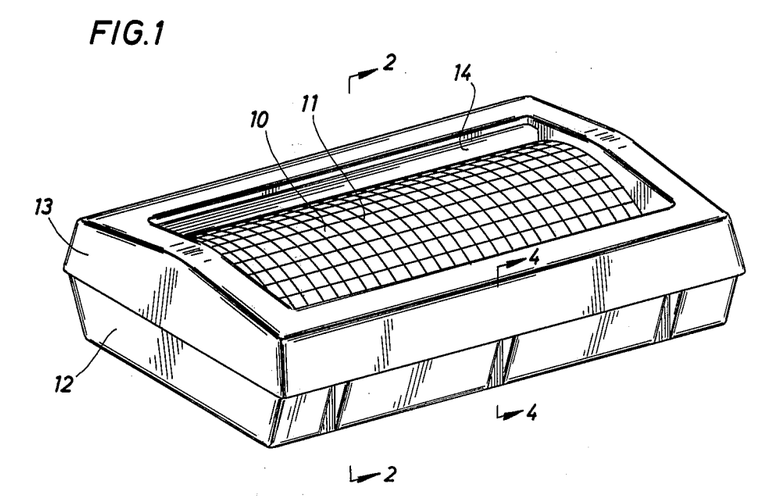
FIG. 1 is an outer view of a preferred wet trap according to the invention.

Referring to FIG. 1, flies are attracted to a sloped target area 10 covered with a closely fitting or flush grill 11. The base section, which is divided into a lower portion 12 and an upper portion 13, surrounds the bottom and sides of target area 10 forming a cavity 14 for the containment and concealment of intoxicated flies.

Figure 2:
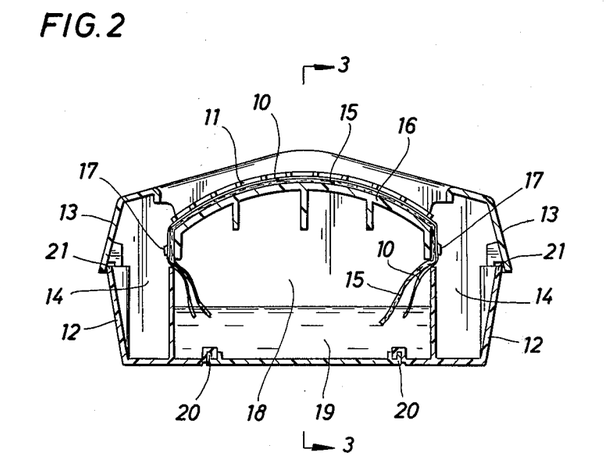
FIG. 2 is a cross-section of the wet trap from line 2—2 of FIG. 1.
Figure 3:
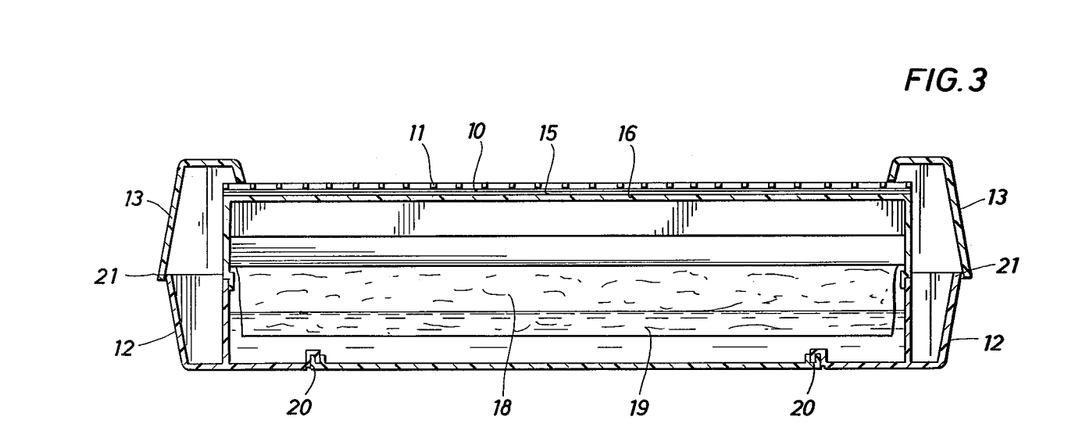
FIG. 3 is a cross-sectional view of the length of the trap taken along line 3—3 of FIG. 2.
Figure 5:
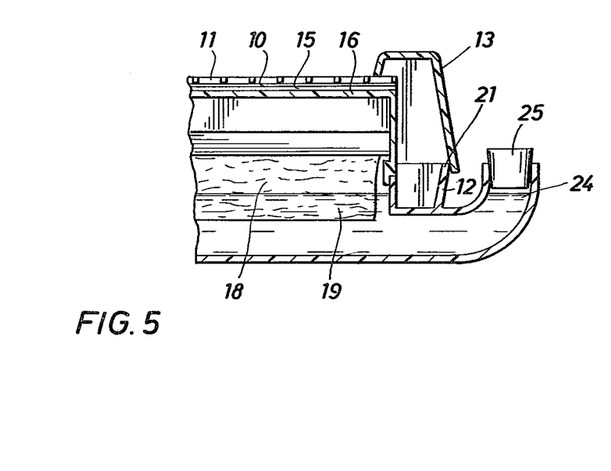
FIG. 5 is a partial cross-sectional view of the preferred wet trap of FIG. 1, showing an alternative embodiment of an inlet or portal for adding liquid to the fluid reservoir of the device.

Referring to FIGS. 2, 3 and 5, a water-wicking material 15 and rigid plastic supporting member 16 are layered under the target area 10 and flush grill 11. The plastic supporting member 16, whose convex side determines the configuration of the target area 10, is attached at its ends to the upper portion 13 of the base section. The target area 10 and water-wicking material 15 are held in place by means of hooks 17 extending out from plastic supporting member 16. The concave side of the plastic supporting member 16 defines the top of the hollow interior 18 of the base section, the lower portion of which further acts as a fluid reservoir for liquid 19. Sufficient clearance along the sides of the plastic supporting member 16 exists such that the water-wicking material 15 and target area 10 may extend downward into the hollow interior 18 and establish fluid contact with the liquid 19. The sides 12 and 13 of the base section extend upward to form a cavity 14 for containment and concealment of intoxicated flies between the sides of the base section and the plastic target area supporting member 16. The level of liquid 19 in the fluid reservoir 18 may be maintained by additions through the resealable inlet or portal 20. The lower portion 12 and upper portion 13 of the base section are joined together by a clip or fastener 21.

Figure 4:
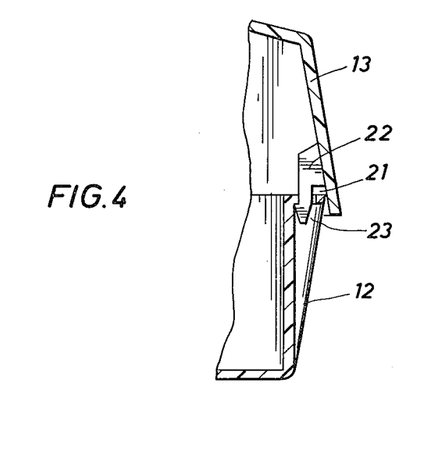
FIG. 4 is an enlarged partial cross-sectional view of an embodiment of the base portion of the device from line 4—4 of FIG. 1.

Referring to FIG. 4, a clip or fastener 21 shown in FIGS. 2 and 3 is detailed. The clip or fastener 21 contains a male member 22 attached to the upper portion 13 of the base section and a female member 23 attached to the lower portion 12 of the base section. The male member 22 is held in the female member 23 by means of tension, thereby holding the upper portion 13 and lower portion 12 of the base tightly together.

Referring to FIG. 5, the wet trap may be modified to contain an inlet or portal 24, resealable with stopper 25, for maintenance of the level of liquid 19 in the fluid reservoir 18.

Figure 6:
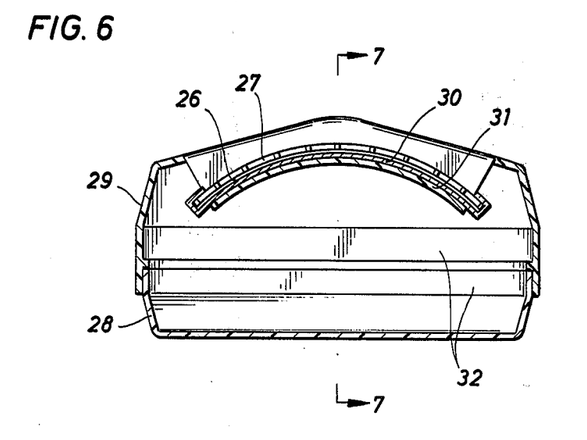
FIGS. 6 and 7 are cross-sections taken along the width and length of a preferred dry trap according to the invention. The cross-section in FIG. 7 is from line 7—7 of FIG. 6. The dry trap has an external configuration substantially similar to that shown in FIG. 1 for the wet trap.
Figure 7:
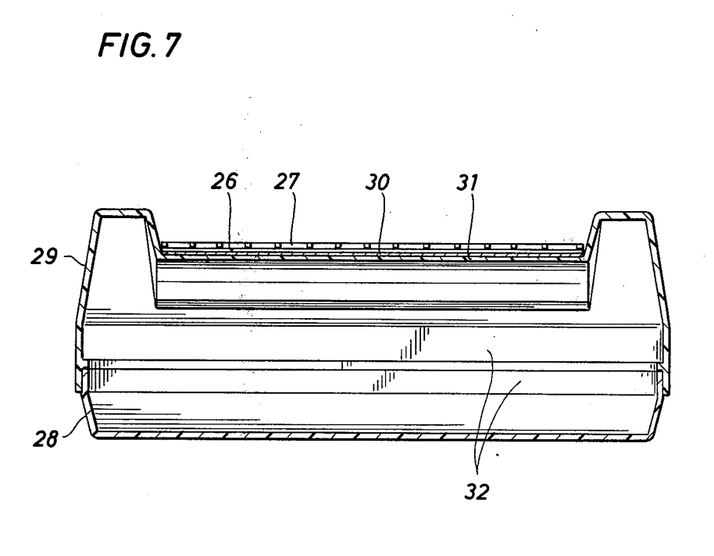

Referring to FIGS. 6 and 7, which illustrate a preferred dry trap, the plastic base section is again divided into a lower portion 28 and upper portion 29. The target area 26 and flush grill 27 are layered above and held in place by a metal area target holder 30. The concave side of the target area holder 30 adheres to and is supported by the convex side of the recessed plastic support 31. The plastic support 31 is attached at its ends to the upper portion 29 of the base section; a cavity 32 for the containment and concealment of intoxicated flies is formed thereby, with its top defined by the concave side of the recessed plastic support 31 and its bottom defined by the bottom of the lower portion 28 of the base section. The intoxicated flies roll down the sloped target area 26 into said cavity 32, since there is sufficient clearance between the perimeter of the plastic support 31 and the sides of the device for the flies to so descend into cavity 32.

The invention is further illustrated in the following examples, which are not to be construed as limiting its scope.

EXAMPLE 1

The insecticidal activity of various nitromethylene heterocycles against the house fly (*Musca domestica*) were determined by directly spraying the insects in a wind tunnel. The compounds tested correspond to the formula:

(I)

wherein X and Y have the meanings shown in the table below. The compound of the invention, namely tetrahydro-2-(nitromethylene)-2H-1,3-thiazine, corresponds to formula (I), wherein X and Y are both hydrogen. The results are expressed in terms of a toxicity index where the compound tested is compared to the activity of parathion against the house fly in the same testing device.

| X | Y | Toxicity Index (Parathion = 100) |
|---|---|---|
| H | H | 161 |
| Br | H | 59 |
| Cl | H | 14 |
| CH(OH)CCl$_3$ | H | 35 |
| C(O)CH$_3$ | H | 15 |
| CH$_2$CH=CH$_2$ | H | 7 |
| H | CH$_3$ | 0.8 |
| H | CH$_2$CH$_3$ | 1.4 |
| H | CH$_2$CH$_2$CH$_3$ | 0.6 |

EXAMPLE 2

The physical properties of TNMT were evaluated and were found to be as follows:

| | |
|---|---|
| Melting point, °C. | 78 |
| Solubility, % weight/volume | Water, 20 |
| | Acetone, 7 |
| Hydrolytic Stability (half life) | 3 hours at pH 1.1 |
| | over 3 months at pH 7.0 |
| | 13 days at pH 9.1 |
| Photochemical Stability (half life, 350 nm simulated sunlight, 100ppm) | Water, 10 minutes |
| | CH$_2$Cl$_2$, 1 minute |

This data was obtained via standard laboratory methods and not from tests of the compound in the device of the invention.

EXAMPLE 3

To determine the response of house flies to color, eight cotton pads, 10×5 centimeters, were dyed with solutions of dyes in water/glycerine (90:10). Excess water/glycerine was squeezed out, 100 mg of TNMT were sprinkled on the surface and the pads placed in 14 cm. Petri dish lids on a rotating turntable located in a Peet-Grady chamber. The chamber was lit by a single incandescent bulb; various background colors and temperatures of approximately 28° C. were used. The number of dead flies associated with each color was counted after 18 hours; 500 mixed sex flies were used and each combination was tested three times. The data were subjected to an analysis of variance (95% confidence limit); the superscripts represent colors that are statistically equivalent.

| | Percent Insects Associated with Background Colors | | |
|---|---|---|---|
| Trap Colors | White | Grey | Black |
| Black | 22[d] | 27[d] | 12[a] |
| Green | 9[ab] | 13[bc] | 19[b] |
| Yellow | 5[a] | 5[a] | 9[a] |
| Orange | 18[c] | 11[abc] | 12[a] |
| White | 7[a] | 10[ab] | 13[ab] |
| Red | 15[bc] | 15[c] | 11[a] |
| Violet | 7[a] | 10[abc] | 11[a] |
| Blue | 16[cd] | 8[ab] | 14[ab] |

The results indicate the optimum color combination to be a black toxicant-containing surface surrounded by a white or grey background.

EXAMPLE 4

A device was constructed comprising a black plastic box (12×7 cm), the top of which was covered by a horizontal metal sheet which supported a layer of blotter paper which was in turn covered with black muslin. Water was added to the box and wicked up via the blotter to the toxicant containing muslin surface. A variety of toxicants were tested in the Peet-Grady chamber against house flies.

| Example | Toxicant | KT$_{50}$(min)[1] | Efficiency (%)[2] |
|---|---|---|---|
| 4a | TNMT (100 mg sprinkled on surface) | 28 | 81 |
| 4b | NUDRIN[R] Insecticide | 104 | 65 |
| 4c | VAPONA[R] Insecticide | 75 | 62 |
| 4d | AZODRIN[R] Insecticide | 66 | 70 |

[1]time required to incapacitate 50% of fly sample
[2]percent of flies found dead within a 12 inch square with device at center (a measure of how quickly the toxicant takes effect).

Standard fly paper (Fly-Catcher; Aeroxon Products, Inc.) was less effective, with an average of 52% of the flies becoming entangled; the remaining free flies in the chamber died of starvation or dehydration within 24 hours. The commercially available NO-PEST ® strip hung in the chamber began to work slowly, with an average of 14% of the flies knocked down at 30 minutes. Although 93% of the flies were knocked down by the strip at sixty minutes, this was in all probability due to a rapid vapor buildup in the small air volume of the chamber.

EXAMPLE 5

A series of devices constructed as in Example 4a were tested in open steer barns. Devices with various surface areas, both with and without the addition of water, were included. Muscalure and/or sugar were incorporated by grinding 0.5 grams of an appropriate bait (0.25% TNMT; 0.13% muscalure; 0.2% dye; 99.42% sugar) and applying it to the surface of a moist trap. Subsequently, 100 milligrams of TNMT were also sprinkled on the surface and the devices dried at ambient laboratory temperatures for twelve hours. The insects collected were almost exclusively house flies consisting of 58% males and 42% females.

| Size | H$_2$O | Sugar | Muscalure | Flies Killed 2.5 hr. | 5 hr | 24 hr |
|---|---|---|---|---|---|---|
| 9 cm$^2$ | X | | | 4 | 7 | 14 |
| 20 cm$^2$ | X | | | 3 | 8 | 8 |
| 84 cm$^2$ | X | | | 14 | 43 | 159 |
| 84 cm$^2$ | X | X | | 36 | 92 | — |
| 84 cm$^2$ | | X | | 25 | 25 | 54 |
| 84 cm$^2$ | | X | X | 83 | 122 | 328 |
| 84 cm$^2$ | X | X | X | 209 | 415 | 1929 |

EXAMPLE 6

A device according to the invention was constructed using a 12×7 centimeter white plastic box with a target area with downwardly sloping curved sides accessible from the top of the device. The target area comprised black paper coated with 2 milligrams per square centimeter of a glaze made up of 13.7% TNMT insecticide, 13.7% polyvinyl pyrollidone and 72.6% corn syrup solids. An attractive dosage of muscalure was subsequently deposited on the target area. The target area had a close fitting plastic grill with 3×4 millimeter holes about 1-3 millimeters from the surface (XN-1670 Plastic Netting, Conwed Corp.).

EXAMPLE 7

A device according to the invention was constructed using a 12×7 centimeter white plastic box with a target area with downwardly sloping curved sides accessible from the top of the device. The base portion contained a water reservoir. The target area comprised black muslin covering a blotter that extended into the reservoir. An appropriate bait (0.5 grams), as in Example 5, was deposited on the target area surface, followed by 100 milligrams of TNMT. Water added to the reservoir would wick up to the toxicant containing surface via the blotter.

EXAMPLE 8

Several of the above devices and adaptations thereof were tested in a steer barn. In all cases the surface area of the active target area was reduced to 52 square centimeters.

| Device | Fly Kill 5 Hourly Randomizations |
|---|---|
| Example 6 | 375 |
| Example 6 | 378 |
| Example 6 painted entirely black | 1091 |
| Example 7 | 541 |

Similar tests were conducted in a smaller animal barn with a less uniform fly population.

| Device | Total Fly Kill | Performance[1] Index | Efficiency |
|---|---|---|---|
| Example 6 | 188 | 3 | 77 |
| Example 6 | 239 | 4 | 79 |
| Example 6 (painted entirely black) | 387 | 6 | 70 |
| Example 6 (painted entirely black) | 296 | 4 | 71 |
| Unmounted Glaze Target[2] | 297 | 4 | — |
| Unmounted Glaze Target[2] | 414 | 6 | — |
| Example 4a + Muscalure | 6673 | 100 | — |

[1]Performance Index = $\frac{\text{Mortality with test device} \times 100}{\text{Mortality with Example 4a device with muscalure}}$
[2]Target area from Example 6 without mounting in base portion.

The variations for the models painted entirely black demonstrate that flies are likely attracted to different colors or contrasts in different surroundings. The low Performance Indices for the devices of Example 6 are believed to be due to the fact they compared here to the water-containing device of Example 4a, during an autumn test when flies appeared to have an unusually high attraction to moisture.

EXAMPLE 9

A number of the devices constructed as above were tested against predominantly house flies in a dairy barn and a piggary at approximately 31° C. and a relative humidity of approximately 42%. In all cases the target area surface was 52 square centimeters.

| Device | Dairy Barn Performance Index[1] | Piggary Performance Index[1] |
|---|---|---|
| Example 4a | 72 | 43 |
| Example 4a + Muscalure | 100 | 100 |
| Example 6 | 31 | 77 |
| Modified Example 7[2] | 151 | 74 |
| Tugon Bait[3] | 38 | — |
| Fly Paper | — | 8 |

[1]Performance Index = $\frac{\text{Mortality with test device} \times 100}{\text{Mortality with Example 4a device with muscalure}}$
[2]Similar to device of Example 7, with the exception that the sugar bait was not used and the muscalure was deposited on the target area directly using a pipette.
[3]Contains 0.25% VAPONA ® insecticide and 2.0% trichlorophon. Used for comparison.

The data suggest that the presence of water improves performance. The device of Example 6 yielded Performance Indices of from zero to 122 in tests at these and other locations. The same device also gave Performance Indices which varied by a factor of ten according to the season when tested. These devices are therefore subject to wide variations in performance, depending on location as well as the temperature and humidity accompanying various seasons. Their performance is thought to depend also on the fly population, types of flies (including species and wild versus cultured varieties) and placement of the devices.

EXAMPLE 10a

A device similar to that in Example 6 was constructed, but contained 42 mg of TNMT insecticide and was enlarged so as to contain a target area surface of 94 square centimeters. No plastic grill was used to cover the target area.

EXAMPLE 10b

A device similar to that in Example 7 was constructed, but contained 42 mg of TNMT insecticide and was enlarged so as to contain a target area surface of 94 square centimeters. No plastic grill was used to cover the target area.

EXAMPLE 11

The devices of Example 10 were compared with other devices in hotel room tests with controlled numbers of flies in late spring in California. Eight independent tests of each device were made, using each device twice in each room. Room temperatures averaged 24° C. Raw mortality data after a 24 hour test was used to calculate binomial probability distributions; comparisons were then made by statistically testing a hypothesis that there existed no difference between the pairs tested. The following results were obtained:

(a) the device of Example 10b is as effective as the device of Example 4a with muscalure, despite the larger amount (100 mg) of insecticide contained in the latter.

(b) the device of Example 10a is as effective as the device of Example 6 altered to contain 42 mg of insecticide and a target area surface of 52 square centimeters. The same amount of insecticide is used in both of these devices, although the surface concentration is lower in the larger device of Example 10a.

(c) three devices of Example 6, altered to each contain 42 mg of insecticide and a target area surface of 52 square centimeters, are roughly equivalent in performance to one device of Example 4a with muscalure. Performances were found to vary according to placement of the devices within each room.

EXAMPLE 12

The hotel room tests conducted as in Example 11 were repeated in the summer (July) when wild fly activity is higher. Similar statistical analyses gave the following results:

(a) the device of Example 10a showed better performance in the spring tests than the summer tests. This was thought to be due to the increasing need of the flies for water in the summer months.

(b) the device of Example 10b appeared in one test to show equal performance in the summer and spring but appeared in another test to show better performance in the summer.

(c) the device of Example 10b showed performance superior to the other devices tested, i.e. devices of Examples 4a with muscalure, 10a, and devices of Examples 6 and 7, altered to each contain 42 mg of insecticide and a target area surface of 52 square centimeters.

EXAMPLE 13

The effect of accelerated storage (storage at 49° C. in open air with full air circulation) was tested on a 52.25 square centimeter black paper target area coated with an aqueous solution of 1 part TNMT insecticide, 1 part PVP and 6 parts corn syrup, so as to contain about 10 mg of insecticide. The results were determined using a one cubic foot cage containing 100 flies.

| Days of Storage | $KT_{50}(min.)$[1] | mg of TNMT remaining |
|---|---|---|
| 0 | 21 | 10 |
| 7 | 21 | — |
| 21 | 22 | 2.76 |
| 56 | — | 0.69 |
| 70 | 27 | — |
| 84 | 30 | — |

A similar target area was tested for the effect of exposure to sunlight through glass. The target areas were placed on the west side of a greenhouse and received diffuse sunlight through whitewashed glass until early afternoon and sunlight through clean glass from 2 p.m. to sundown.

| Days of Exposure | $KT_{50}(min.)$[1] | mg of TNMT remaining |
|---|---|---|
| 0 | 21 | 10 |
| 2 | 34 | 3.1 |
| 7 | 32 | 0.52 |
| 28 | 46 | — |
| 39 | — | 0.51 |
| 53 | 80 | — |
| 84 | 220 | — |

[1]Time required to incapacitate 50% of fly sample.

What is claimed is:
1. A device for combatting flies comprising:
  (a) a target area of porous material comprising a sloped surface containing a dosage of tetrahydro-2-(nitromethylene)-2H-1,3-thiazine insecticide lethal to flies,
  (b) a closely fitting grill covering said target area but allowing contact by the flies thereon,
  (c) a sloped supporting member for said target area comprising a solid sheet of rigid impermeable material shaped to conform with the shape of the target area and having its upper surface affixed to the target area so as to support and define the configuration of the target area,
  (d) a hollow base section having a bottom and side or sides surrounding the bottom and perimeter of said sloped target area supporting member, the side or sides of said base section extending up a sufficient distance to form a cavity between the side or sides of the base section and the target area supporting member, said cavity being of sufficient size for the containment and concealment of intoxicated flies; the base section being attached to the sloped supporting member such that a refillable reservoir for fluid storage or containment is formed in the hollow base section, said reservoir being defined on its top by the sloped supporting member and on its bottom by the bottom of the base section, and
  (e) a means of establishing fluid contact between said target area and said refillable reservoir.

2. A device as defined in claim 1, wherein the means of establishing fluid contact between the target area and the fluid reservoir in the base is an extension of the target area material and a water-wicking material layered between the supporting member and the target area downward into the fluid reservoir to a point below the fluid level present when liquid is added to the fluid reservoir.

3. A device as defined in claim 1, wherein the cavity for containment and concealment of intoxicated flies extends around the entire perimeter of the target area supporting member.

4. A device as defined in claim 1, wherein the cavity for containment and concealment of intoxicated flies is defined on its bottom by the bottom of the base section.

5. A device as defined in claim 1, wherein the upper portion of the side or sides of the base section bends inwardly to form a lip that further conceals flies in the cavity for the containment and concealment of intoxicated flies.

6. A device as defined in claim 1, wherein the base section is rectangular or box shaped.

7. A device as defined in claim 1, wherein an attractive dosage of fly sex attractant is additionally deposited on the target area.

8. A device as defined in claim 2, wherein an attractive dosage of a fly sex attractant is additionally deposited on the target area and a foodstuff or bait acceptable to flies is additionally deposited on the target area.

9. A device as defined in claim 8, wherein the fly sex attractant comprises muscalure and the foodstuff or bait comprises sugar.

10. A device as defined in claim 1, wherein the means of establishing fluid contact between the target area and the fluid reservoir in the base is an extension of the target area material downward into the fluid reservoir to a point below the fluid level present when liquid is added to the fluid reservoir.

11. A device as defined in claim 10, wherein an attractive dosage of a fly sex attractant is additionally deposited on the target area and a foodstuff or bait acceptable to flies is additionally deposited on the target area.

12. A device as defined in claim 1, wherein the means of establishing fluid contact between the target area and the fluid reservoir in the base is an extension of a water-wicking material layered between the supporting member and the target area downward into the fluid reservoir to a point below the fluid level present when liquid is added to the fluid reservoir.

13. A device as defined in claim 12, wherein an attractive dosage of a fly sex attractant is additionally deposited on the target area and a foodstuff or bait acceptable to flies is additionally deposited on the target area.

* * * * *